(12) United States Patent
Fujimoto et al.

(10) Patent No.: US 9,393,443 B2
(45) Date of Patent: Jul. 19, 2016

(54) TREATMENT PLANNING SYSTEM

(71) Applicant: HITACHI, LTD., Tokyo (JP)

(72) Inventors: Rintaro Fujimoto, Hitachinaka (JP); Yoshihiko Nagamine, Hitachi (JP); Yusuke Fujii, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 350 days.

(21) Appl. No.: 13/951,621

(22) Filed: Jul. 26, 2013

(65) Prior Publication Data

US 2014/0031602 A1 Jan. 30, 2014

(30) Foreign Application Priority Data

Jul. 30, 2012 (JP) .................. 2012-167903

(51) Int. Cl.
*A61N 5/00* (2006.01)
*A61N 5/10* (2006.01)

(52) U.S. Cl.
CPC ............ *A61N 5/1037* (2013.01); *A61N 5/1043* (2013.01); *A61N 5/1031* (2013.01); *A61N 2005/1087* (2013.01)

(58) Field of Classification Search
CPC ........ A61N 5/00; A61N 5/10; A61N 5/10375
USPC .......................................... 600/1–8
See application file for complete search history.

(56) References Cited

U.S. PATENT DOCUMENTS

2008/0071131 A1   3/2008  Rietzel
2009/0095921 A1   4/2009  Bert et al.

FOREIGN PATENT DOCUMENTS

| EP | 1 900 392 A1 | 3/2008 |
| EP | 1 905 482 A1 | 4/2008 |
| JP | 2008-080131 A | 4/2008 |
| JP | 2009-502257 A | 1/2009 |

*Primary Examiner* — John Lacyk
(74) *Attorney, Agent, or Firm* — Mattingly & Malur, PC

(57) ABSTRACT

A treatment planning system is provided which, with irradiation parameters varied over time, performs highly accurate dose distribution calculations based on information about tumor movements included in 4D CT images. The system is characterized by the ability to read CT images furnished with timing information and associate the status of the irradiation target corresponding to an elapsed time from the beginning of irradiation with positions being irradiated at corresponding elapsed time points so as to calculate the dose distribution.

11 Claims, 14 Drawing Sheets

TREATMENT PLANNING SYSTEM

BACKGROUND OF THE INVENTION

1. Field of the Invention

The present invention relates to a treatment planning system. More particularly, the invention relates to a treatment planning system for use with radiation therapy equipment that applies ion beams such as X-rays and proton beams to the tumor for treatment.

2. Description of the Related Art

In recent years, radiation therapy aimed at applying various types of radiation to tumor cells to induce their necrosis has been practiced extensively. The radiation in use is not limited to the most commonly used X-rays; particle beams such as proton beams are gaining widespread acceptance for treatment.

The irradiation technology for handling radiation has been highly developed. Progress has been made in the development of techniques for enhancing dose concentration on the tumor while minimizing adverse effects on the normal organs around the affected part. In a treatment using X-rays called IMRT (Intensity Modulated Radiation Therapy), the tumor is irradiated in multiple directions while the collimator shape is being varied. This makes it possible to irradiate the target region of a complicated shape while minimizing the irradiation dose on the surrounding normal tissues. Also utilized is a method that involves rotating a gantry equipped with an irradiation device to irradiate the tumor continuously while the collimator shape is being changed.

In particle therapy, the scanning irradiation method is getting widespread acceptance. This method involves irradiating the inside of the tumor in a manner filling it with fine particle beams so that a high dose is given only to the tumor region. Basically, there is no need for instruments specific to the patient such as the collimator for shaping dose distribution in keeping with the tumor shape; diverse kinds of dose distribution can be formed by this method.

Radiation therapy requires that detailed plans be made beforehand with regard to the irradiation position and tumor status. The irradiation dose and irradiation position are determined in such a manner that the treatment planning system provides a desired does distribution regarding the tumor and its surroundings in advance. Upon advance planning, the conditions in the patient's body are verified most commonly by means of X-ray CT images (called the CT images hereunder). The position of the tumor is designated and the calculations of the dose distribution inside the body are performed very frequently using the CT images.

Although irradiation should preferably be carried out as planned, there can occur errors in practice due to diverse causes. Such errors are attributable not only to the equipment itself and positioning procedures but also to tumor movements under irradiation caused by respiration and heartbeat. Because the tumor movements typically triggered by respiration and heartbeat differ from patient to patient and from one target region to another, they are difficult to evaluate. In IMRT and scanning irradiation, the desired dose distribution is formed by superimposition of complex distribution patterns, so that variations in the distribution induced by respiration and other movements are particularly difficult to predict.

There has been conceived a method aimed at evaluating quantitatively the effects of the tumor movements on the dose distribution by supplementing the CT images with time-varying information to predict movements of the internal organs around the tumor. The CT images furnished with timing information are called four-dimensional (4D) CT images. Starting from an image representing the state of a moving object in a short time range, 4D CT images are formed by a plurality of sets of 3D CT images taken at different points in time.

For example, the ordinary CT image of respiratory movements is an image that time-averages the movements in the respiratory cycle. The method above involves having 3D CT images obtained at various points in time such as in the inhaled state and exhaled state during the respiratory cycle.

There have been several attempts at predicting the effects of tumor movements on the dose distribution calculations using 4D CT images in conjunction with the treatment planning system. For example, JP-2008-80131-A discloses that given a plurality of phases included in 4D CT images, the dose distribution is calculated from the weight of each of the phases. JP-2009-502257-T discloses that given information about the respiratory state recorded during radiation irradiation, one of the phases in the corresponding 4D CT images is selected and the dose distribution is calculated regarding the selected phase.

The dose distribution calculated for each of the phases involved can be integrated by means of the non-rigid registration technique as referenced in the above-cited patent literature. The body structure such as the target region between different phases varies not only in position but also in shape. According to the non-rigid registration technique, with the CT image of a given phase (e.g., exhaled phase) taken as the reference CT image, different points within the target in the reference CT image can be made to correspond to their corresponding positions in the CT images obtained from the other phases. By integrating the doses at these corresponding points, an ultimate dose distribution on the reference CT image can be acquired.

As described above, the dose calculation techniques using 4D CT images are primarily based on calculating the dose distribution on the CT images of various phases and integrating the distributed doses so as to compute the dose distribution for treatment in a moving state expressed by the 4D CT images.

SUMMARY OF THE INVENTION

However, the dose distribution is affected by the relations between tumor movements and irradiation parameter variations with regard to irradiation methods such as: the scanning method in radiation therapy in which the irradiation parameters such as the angle of the gantry during irradiation of beams, the points receiving the beam irradiation, and the intensity of the beams vary over time from the beginning of irradiation. With the scanning irradiation method, the position and energy of irradiation vary continuously during irradiation that typically lasts several minutes per patient. It is thus necessary to perform dose distribution calculations by associating beam status at different points in time during irradiation on the one hand and the tumor movements on the other hand.

Whereas the 4D CT images include those corresponding to a plurality of phases, if the interval between the phases is not finely defined, there may not always exist a CT image reflecting a known phase corresponding to the radiation irradiated at a given point in time. When the closest phase is selected for dose calculations as with ordinary methods, it might happen that a CT image of a different phase is selected for the calculations even though the positions adjacent to each other are to be irradiated with radiation. In such a case, adding up the calculations about the two phases can result in unintended irregularities of the dose distribution.

An object of the present invention is to provide a treatment planning system for use with radiation therapy equipment of which the irradiation parameters vary over time, the system performing highly accurate dose distribution calculations based on the information about tumor movements included in 4D CT images.

In carrying out the present invention and according to one embodiment thereof, there is provided a treatment planning system including: an input device which inputs parameters for irradiation with radiation; a calculation device which calculates a treatment plan based on the result of the input to the input device; a display device which displays the treatment plan, and a storage unit which stores a series of three-dimensional CT images holding information about variations of a target region to be irradiated with the radiation. After associating the series of three-dimensional CT images with information about elapsed time from beginning to end of a radiation treatment based on the treatment plan, the calculation device interpolates the information about the variations of the target region from the information about the elapsed time and from the series of three-dimensional CT images over each of time periods during which the radiation is applied. The calculation device further calculates a dose distribution based on the interpolated information about the variations of the target region.

Effect of the Invention

For use with radiation therapy equipment of which the irradiation parameters vary over time, there can thus be provided a treatment planning system that performs highly accurate dose distribution calculations based on the information about variations of a target region included in 4D CT images.

More specifically, the tumor movements that vary over time from the beginning of a treatment are associated with the irradiation parameters of a radiation irradiation device, so that the accuracy in performing dose distribution calculations regarding a moving target may be improved.

DESCRIPTION OF THE PREFERRED EMBODIMENTS

First Embodiment

Figure 3:
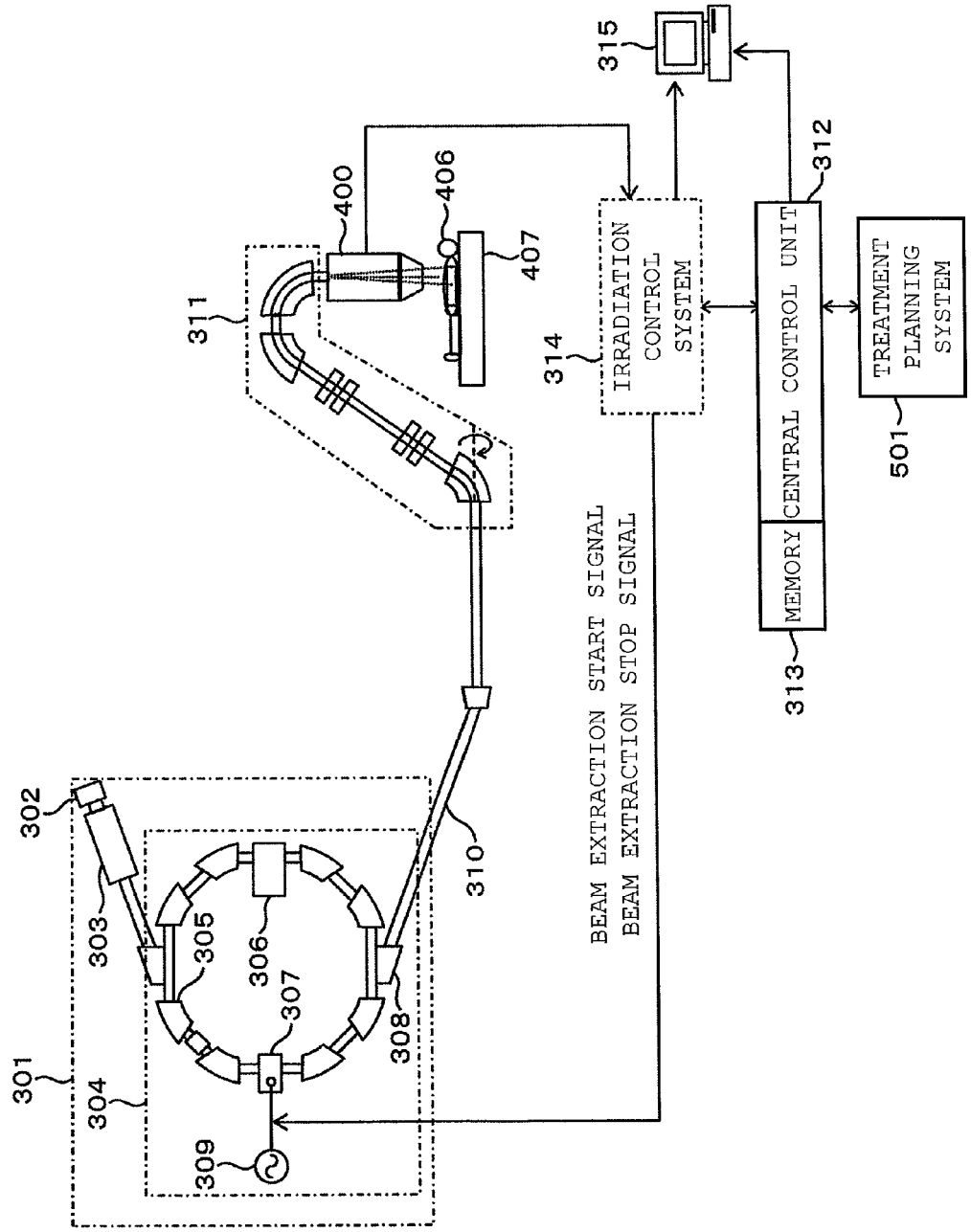
FIG. 3 is an explanatory view showing an overall configuration of a particle therapy system.
Figure 4:
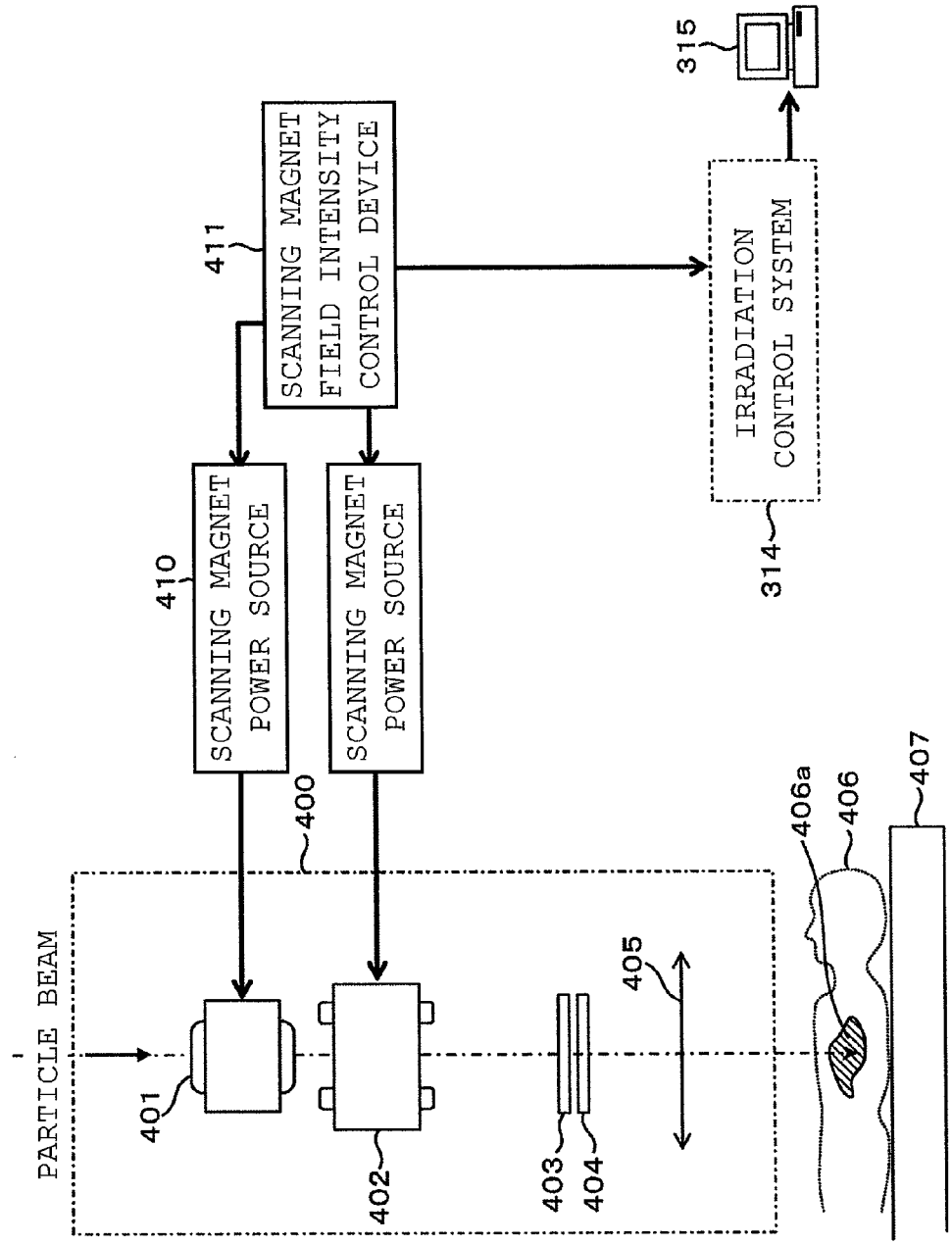
FIG. 4 is an explanatory view showing a structure of a beam delivery system.

As one preferred embodiment of the present invention, a treatment planning system will now be explained in reference to the accompanying drawings. This invention is targeted to provide the treatment planning system such as an X-ray treatment system or a particle therapy system. Explained below with reference to FIGS. 3 and 4 is a particle therapy system as one example of the embodiment. This invention can also be applied to an X-ray treatment system and still provides advantageous effects similar to those of the particle therapy system.

FIG. 3 shows an overall configuration of the particle therapy system. In FIG. 3, the particle therapy system includes a ion beam generation device 301, a high-energy beam transport line 310, a gantry 311, a central control unit 312, a memory 313, an irradiation control system 314, a display device 315, a beam delivery system (irradiation device) 400, a bed 407, and a treatment planning system 501.

The ion beam generation device 301 is made up of an ion source 302, a preaccelerator 303, and a particle beam accelerator 304. With this embodiment, the particle beam accelerator 304 is assumed to be a synchrotron-type particle beam accelerator. Alternatively, any other particle beam accelerator may be used as the particle beam accelerator 304, including the cyclotron type. As shown in FIG. 3, the synchrotron-type particle beam accelerator 304 includes a bending magnet 305, an accelerator 306, a radiofrequency application device 307 for extraction purposes, an extraction deflector 308, and a quadruple magnet (not shown) set up on the orbit of the accelerator 304.

Explained hereunder in reference to FIG. 3 is how a particle beam is generated by the ion beam generation device 301 using the synchrotron-type particle beam accelerator 304 and extracted to a patient. The particles supplied from the ion source 302 are accelerated by the preaccelerator 303 before being sent to the synchrotron acting as the beam accelerator. The synchrotron is furnished with the accelerator 306 that applies a radiofrequency to a radiofrequency acceleration cavity (not shown) attached to the accelerator 306 in synchronism with a particle beam passing through the accelerator 306 while circulating inside the synchrotron, whereby the particle beam is accelerated. In this manner, the particle beam is accelerated until it reaches a predetermined energy level.

After the particle beam is accelerated to a predetermined energy level (e.g., 70 to 250 MeV), the central control unit 312 causes the irradiation control system 314 to output an extraction start signal. This in turn causes radiofrequency power from a radiofrequency power source 309 to be applied to the particle beam circulating inside the synchrotron by way of an extraction radiofrequency electrode attached to the radiofrequency application device 307, before the particle beam is extracted from the synchrotron.

The high-energy beam transport line 310 connects the synchrotron with the beam delivery system 400. The particle beam extracted from the synchrotron is led through the high-energy beam transport line 310 up to the beam delivery system 400 attached to the gantry 311. The gantry 311 is designed to apply the beam to a patient 406 in any desired directions. The entire gantry 311 can be rotated into any direction around the bed 407 on which the patient 406 is lying.

The beam delivery system 400 is designed to rectify the shape of the particle beam to be ultimately applied to the patient 406. The structure of the beam delivery system 400 varies depending on the irradiation method. While the passive scattering method and the scanning method are two typical irradiation methods, this embodiment adopts the scanning method. The scanning method involves allowing a fine beam transported from the high-energy beam transport line 310 to be applied unmodified to a target in a manner scanning the target three-dimensionally, so that a high dose region may be formed only on the target.

FIG. 4 shows a structure of the beam delivery system 400 supporting the scanning method. Outlined below in reference to FIG. 4 are the roles and functions of the components making up the beam delivery system 400. The beam delivery system 400 includes two scanning magnets 401 and 402, a dose monitor 403, and a beam position monitor 404, arrayed from the upstream down. The dose monitor 403 measures the amount of the particle beam passing through the monitor. The beam position monitor 404 measures the position passing through the monitor. The information from the monitors 403 and 404 enables the irradiation control system 314 to make sure that the planned amount of the beam is applied to the planned positions.

The fine particle beam transported from the ion beam generation device 301 via the high-energy beam transport line 310 has its advancing direction deflected by the scanning magnets 401 and 402. These scanning magnets are set up to generate magnetic field lines perpendicularly to the beam advancing direction. In FIG. 4, for example, the scanning magnet 401 deflects the beam in a scanning direction 405, and the scanning magnet 402 deflects the beam perpendicularly to the scanning direction 405. Using the two magnets allows the beam to be moved into any desired position on a plane perpendicular to the beam advancing direction, so that the beam can be applied to a target 406a.

The irradiation control system 314 causes a scanning magnet field intensity control device 411 to control the amounts of currents flowing through the scanning magnets 401 and 402. The scanning magnets 401 and 402 are supplied with their currents from a scanning magnet power source 410. Magnetic fields are excited by the magnets in accordance with the amounts of the currents so as to set the amounts of deflection of the beam as desired. The relations between the amounts of deflection of the particle beam on the one hand and the amounts of the currents on the other hand are retained beforehand in the form of a table in the memory 313 inside the central control unit 312. The stored relations are referenced as needed.

There are two ways to perform scanning with the beam according to the scanning method. One way is to move and stop the irradiation position repeatedly as a discrete method. The other way is to change the irradiation position continuously. The discrete method is carried out as follows: First, with the irradiation position set on a given point, a predetermined amount of the beam is applied. The irradiated point is called the spot. After the predetermined amount of the beam is applied to the spot, beam irradiation is temporarily stopped, and the amounts of the currents flowing through the scanning magnets are changed preparatory to irradiating the next position. After the amounts of the currents are changed and the movement to the next irradiation position is performed, the beam is again applied. In this case, if the movement of the irradiation position is performed at high speed, i.e., if high-speed beam scanning is made possible, then it is possible to exercise control in a manner keeping the beam unstopped during the movement.

The method of continuously moving the irradiation position involves changing the irradiation position while the beam is being applied. That is, while the amounts of magnetic excitation of the magnets are being continuously varied, the irradiation position is moved with the beam applied to pass through the entire irradiation field. According to this method, the irradiation dose per irradiation position is varied by modulating either or both of the speed of scanning and the amount of the beam current.

Figure 5:
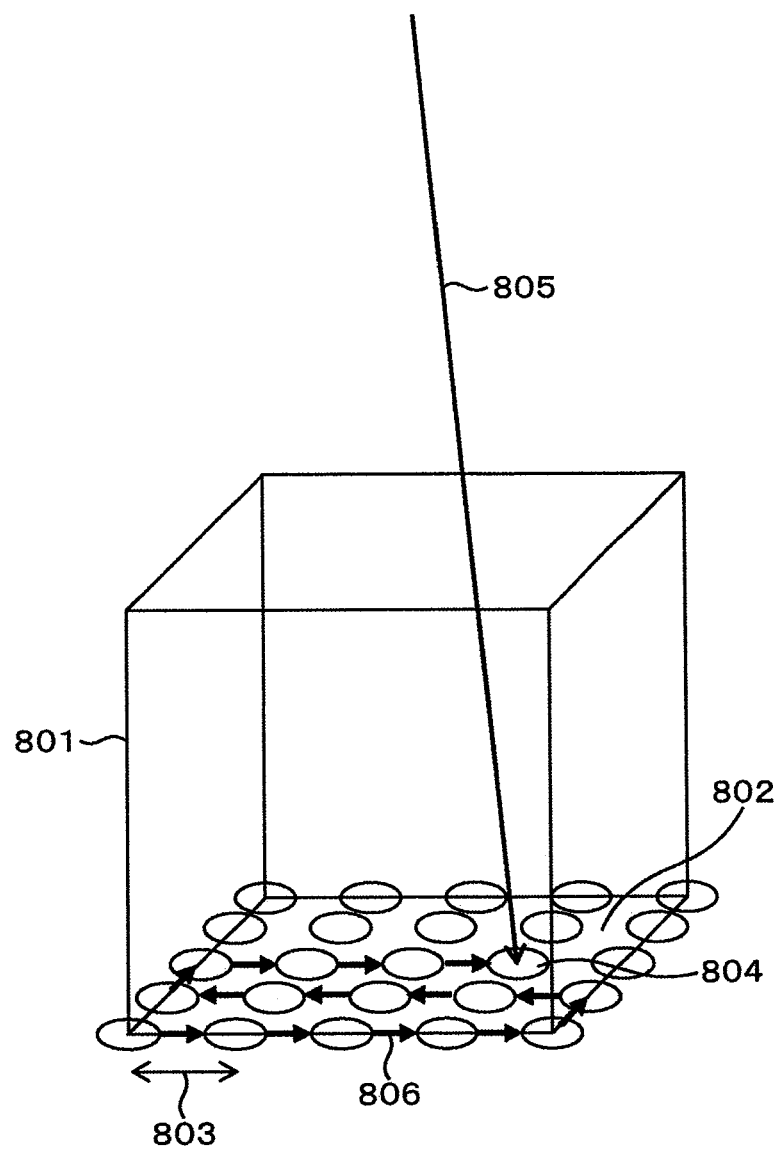
FIG. 5 is a conceptual view showing positions irradiated by the particle beam scanning irradiation method.

FIG. 5 is a conceptual view of irradiation by the discrete method. FIG. 5 shows an example in which a cubic target 801 is irradiated. The particle beam is stopped at a given position in its advancing direction to give most of the energy to that stopped position. For this reason, the energy of the beam is adjusted so that the depth in which the beam is stopped will stay within the target region. Selected in FIG. 5 is a beam whose energy is such that the beam is stopped near a plane 802 irradiated with the same energy. On this plane, discrete beam irradiation positions (spots) are arrayed at spot intervals 803. After one spot has been irradiated with a predetermined dose, the next spot is reached. A spot 804 is irradiated with a beam aimed at that spot 804 and passing through a beam locus 805. After all spots with the same energy arrayed inside the target have been irradiated successively, the depth in which to stop the beam is changed so that positions of another depth inside the target may be irradiated.

In order to change the depth in which the beam is stopped, the energy of the beam applied to the patient 406 is varied. One way of varying the energy is by changing the settings of the particle beam accelerator, i.e., the synchrotron in the case of this embodiment. The particles may be accelerated until they reach the energy level set on the synchrotron. Varying this set value changes the energy applied to the patient 406. In this case, the energy extracted from the synchrotron is varied, so that the energy of the beam passing through the high-energy beam transport line 310 is also changed. This in turn requires changing the settings of the high-energy beam transport line 310. In the case of the synchrotron, it takes about one second to change the energy settings.

Figure 6:
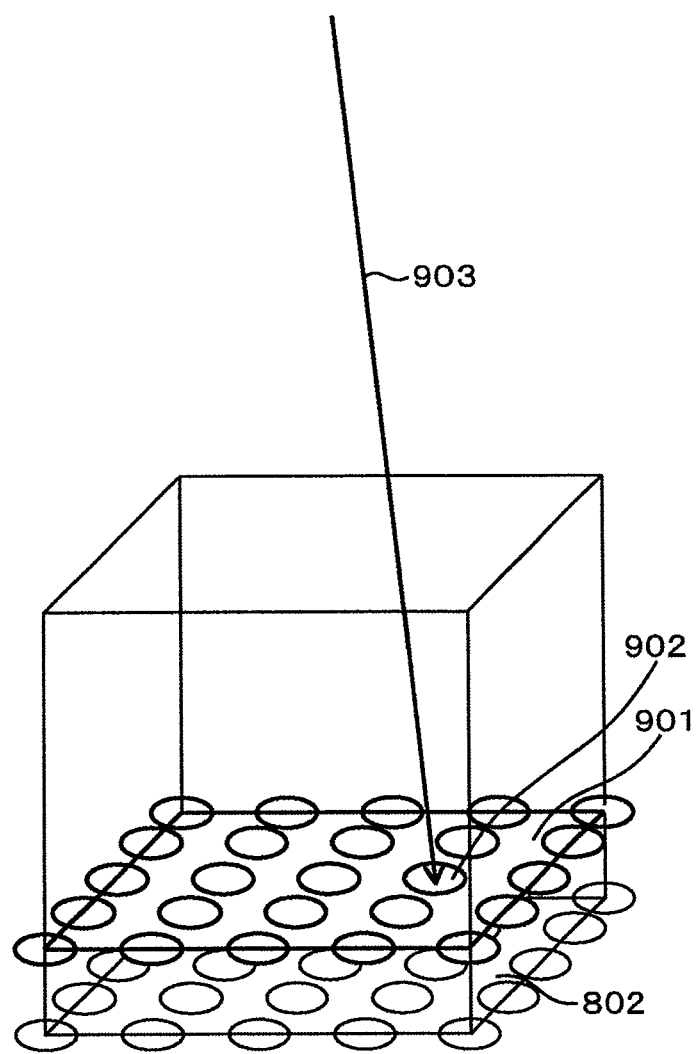
FIG. 6 is a conceptual view showing how the level of energy is changed by the particle beam scanning irradiation method.

In the example of FIG. 5, the energy is given mostly to the region corresponding to the plane 802 irradiated with the same energy. Changing the energy settings brings about the state such as one shown in FIG. 6. In FIG. 6, a beam with an energy level lower than that used in FIG. 5 is applied. The beam is thus stopped at shallower positions. These positions constitute a plane 901 irradiated with the same energy level. A spot 902, one of the spots each corresponding to the beam having this energy level, is irradiated with a beam aimed at that spot 902 and passing through a beam locus 903.

Another method of varying the beam energy involves inserting a range shifter (not shown) into the beam delivery system 400. The thickness of the range shifter is selected in accordance with the changed energy level desired. The thickness may be selected using any of a plurality of range shifters each having a different thickness, or a wedge-shaped opposing range shifter.

Figure 7:
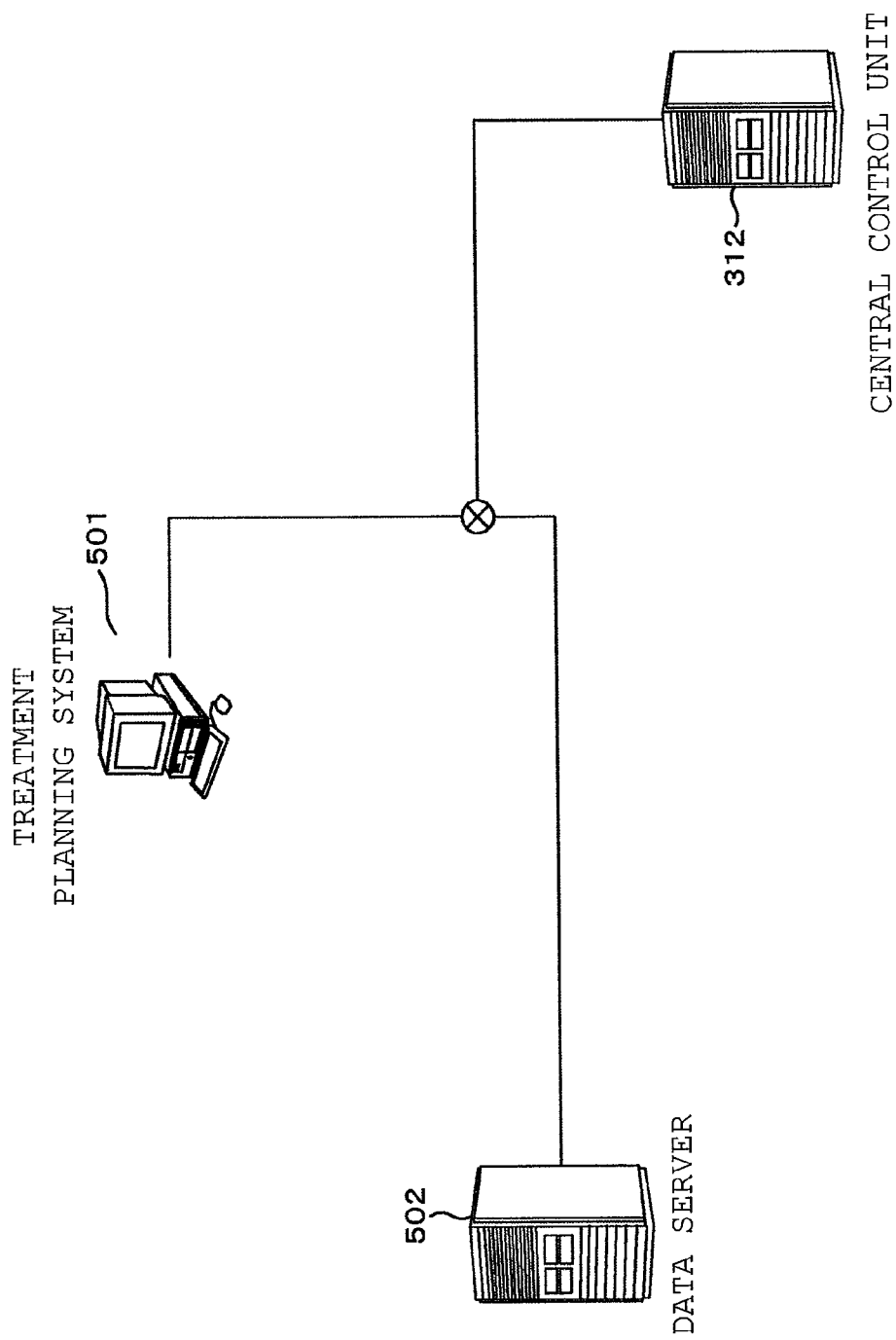
FIG. 7 is an explanatory view showing a structure of a control unit including the inventive device.
Figure 8:
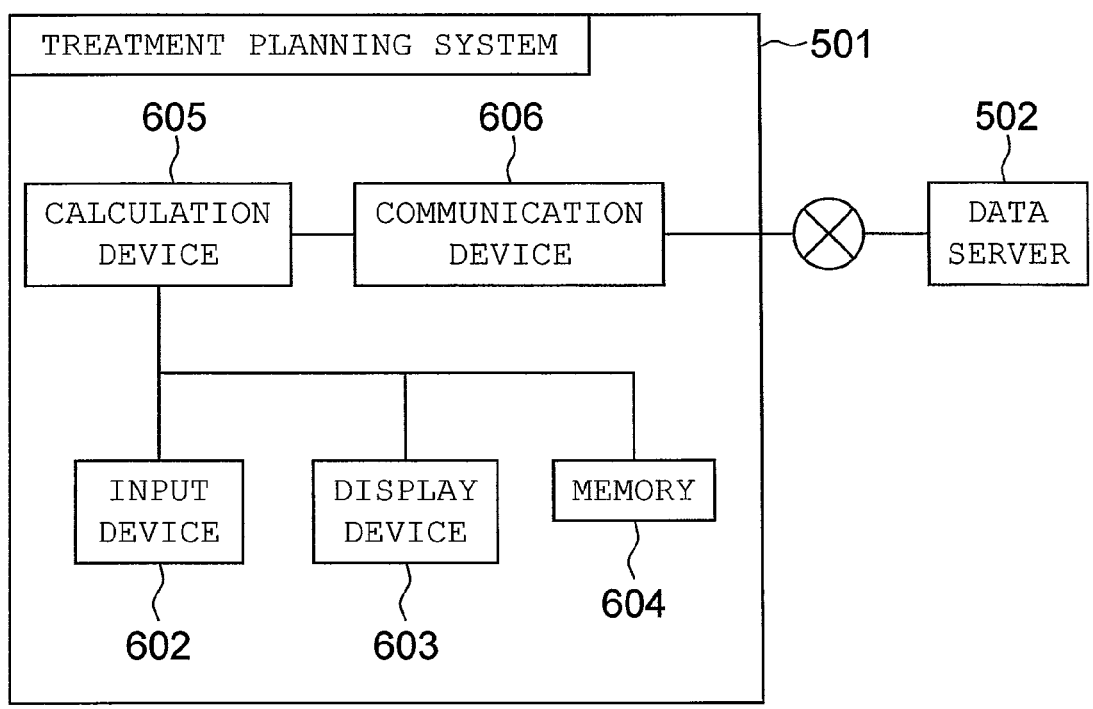
FIG. 8 is an explanatory view showing a structure of the inventive device.

FIG. 7 shows a structure of the treatment planning system 501 as one preferred embodiment of this invention. First of all, the treatment planning system 501 is connected with a data server 502 and the central control unit 312 over a network. As shown in FIG. 8, the treatment planning system 501 includes an input device 602 that inputs parameters for radiation irradiation, a display device 603 that displays a treatment plan, a memory 604, a calculation device 605 (calculation and logic unit) that performs dose distribution calculations, and a communication device 606. The calculation device 605 is connected with the input device 602, display device 603, memory (storage device) 604, and communication device 606.

Figure 1:
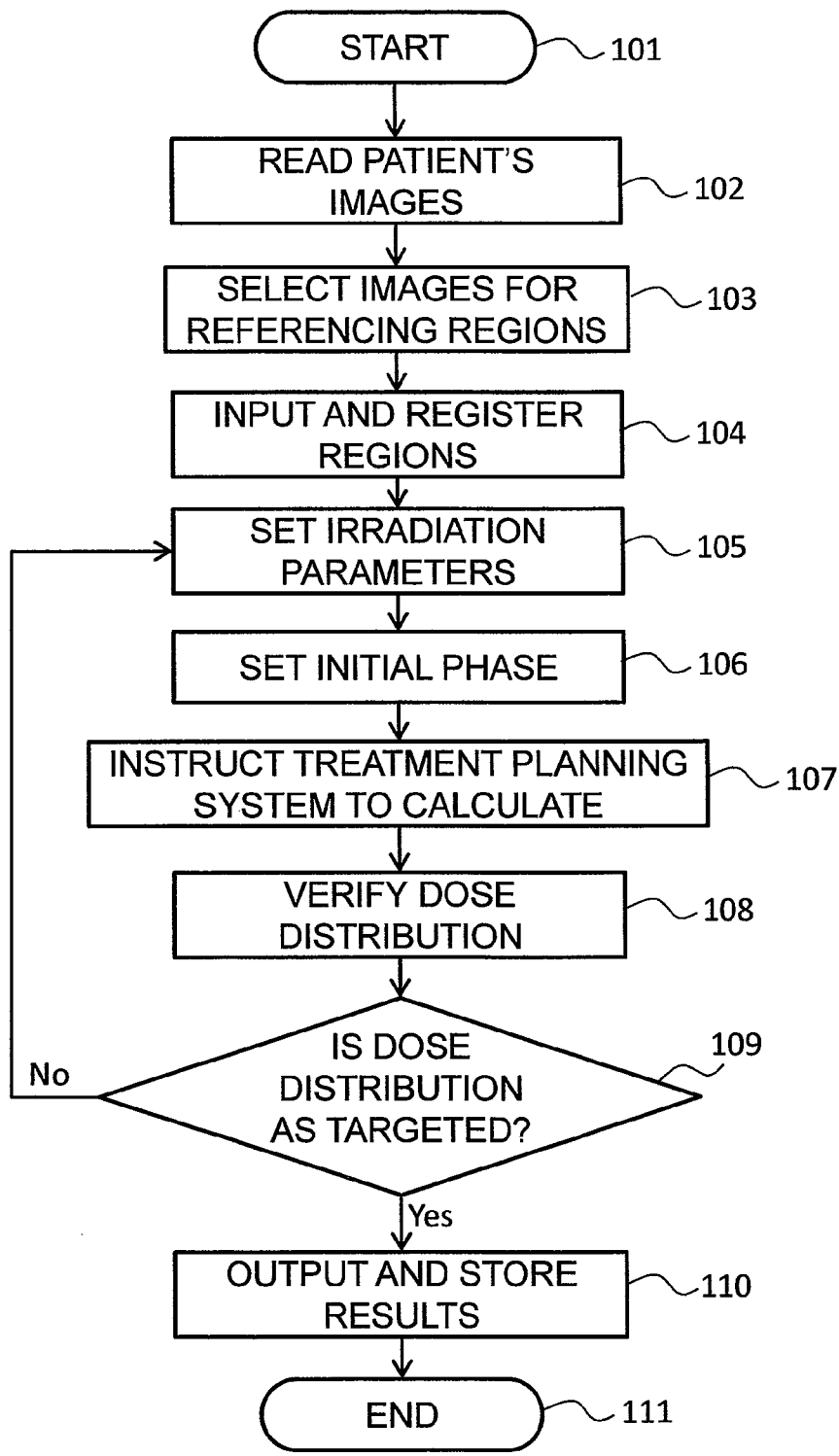
FIG. 1 is a flowchart showing a flow in which a treatment plan is prepared using one preferred embodiment of the present invention.
Figure 2:
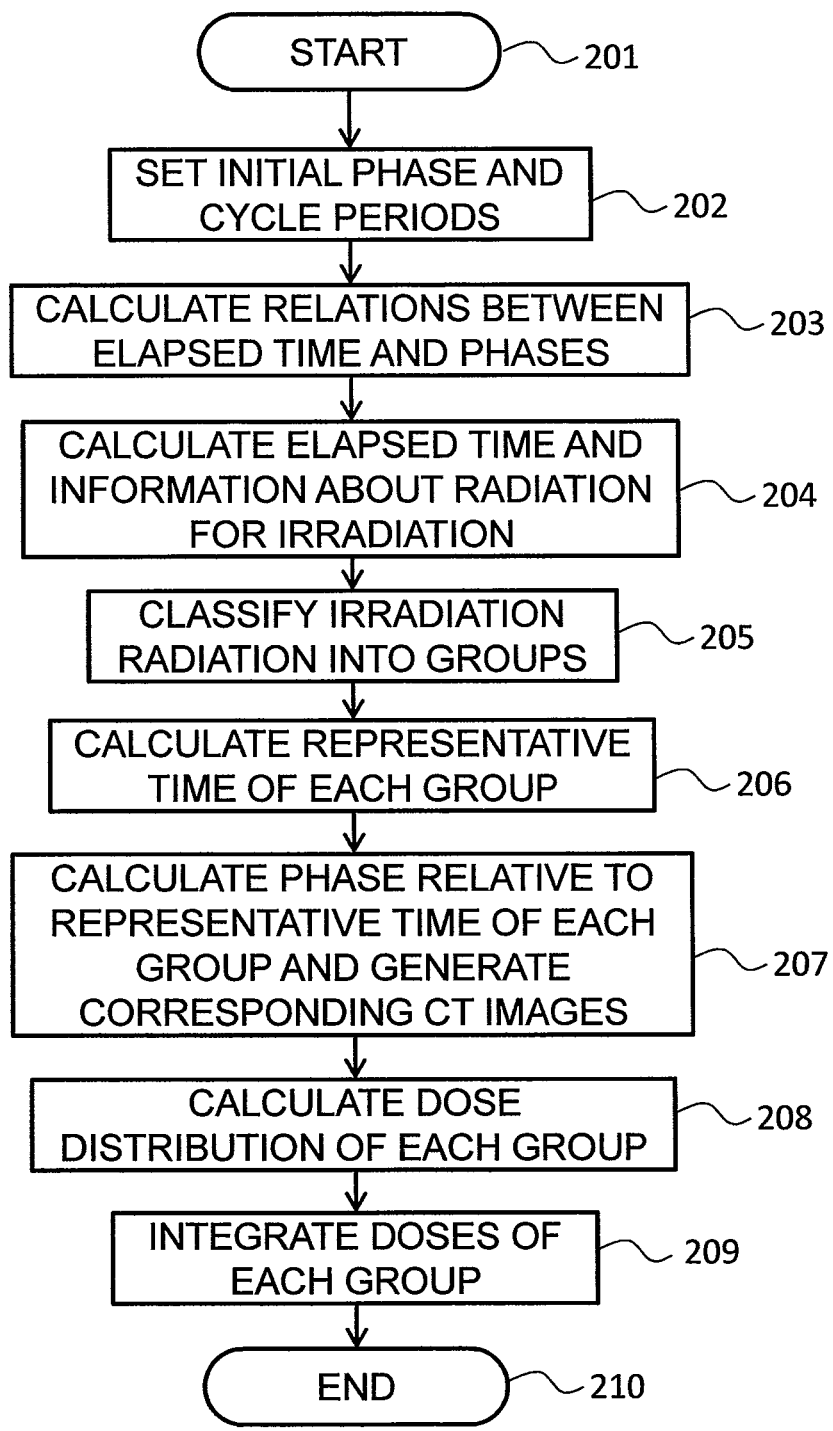
FIG. 2 is a flowchart showing a flow of steps performed by the inventive device of the preferred embodiment.

Explained below in reference to FIGS. 1 and 2 are the flows of operations performed using the treatment planning system 501. FIG. 1 shows a flow of operating steps performed by the operator, and FIG. 2 shows a flow of detailed calculations carried out by the treatment planning system 501 of this embodiment using mainly the calculation device 605.

Prior to the treatment, images for a treatment plan are obtained. The most commonly used images for treatment planning are CT images. The CT images are formed by reconstituting three-dimensional (3D) data based on transparent images obtained in a plurality of directions from a patient. Because this embodiment involves preparing the treatment plan using 4D CT images, the CT images acquired here are also 4D CT images. However, it should be noted that the 4D CT images referenced here are not limited to those obtained by a special imaging method different from that for taking ordinary CT images; the 4D CT images mentioned here represent a set of data composed of a plurality of 3D CT images from different states of the same patient.

The 4D CT images obtained by a CT device (not shown) are stored in the data server 502. The treatment planning system 501 makes use of these 4D CT images. FIG. 1 outlines the flow in which the operator prepares the treatment plan. When preparation of the treatment plan is started (step 101), an engineer (or a doctor) as the operator of this treatment planning system reads the target CT data from the data server 502 using the input device 602 such as a mouse. That is, by operation of the input device 602, the treatment planning system 501 copies the 4D CT images from the data server 502 onto the memory 604 via the network connected with the communication device 606 (step 102).

Figure 9:
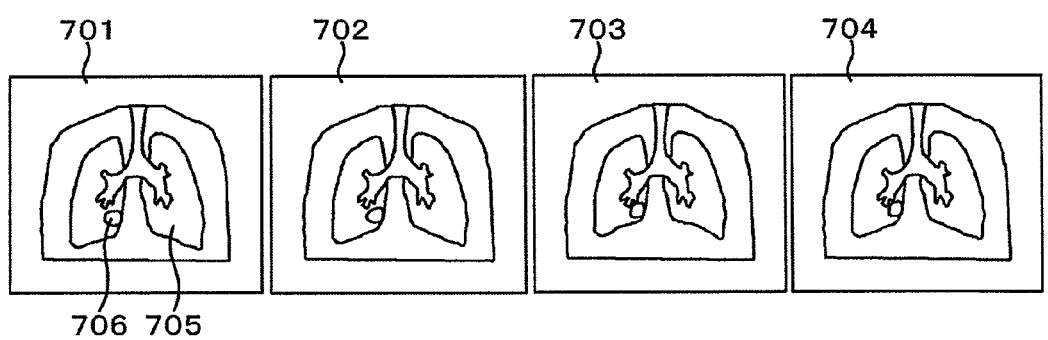
FIG. 9 is a conceptual view showing a structure of 4D CT images.

As mentioned above, the 4D CT images are made up of a set of a plurality of 3D CT images covering the target region and retaining information about the movements of the body structure including translation, rotation, and deformation. With this embodiment, a series of 3D CT images holding such information about the variations of the region irradiated with radiation are called 4D CT images. The individual 3D CT images constituting the 4D CT images entail known temporal relations and indicate different states of the region of interest at different points in time during a given moving cycle (e.g., respiratory or heartbeat cycle). FIG. 9 is a conceptual view showing 4D CT images made up of a first 3D CT image 701 through a fourth 3D CT image 704 (simply called the images 701, 702, 703, and 704 hereunder). In FIG. 9, the four 3D CT images 701 through 704 are shown as 2D CT images for the sake of simplicity.

The individual 3D CT images are those covering the patient's chest region including lungs 705 and a target region 706. The 3D CT images 701 through 704 represent states obtained at four points in time, i.e., CT time 1, CT time 2, CT time 3, and CT time 4, during the patient's respiratory cycle. These images are associated with information identifying each of the states in the respiratory cycle. For example, one respiratory cycle may be divided into a fully inhaled state, a fully exhaled state, and intermediate states (phases), so that the images 701 through 704 may belong to the different phases. Although the 4D CT images are derived from a single moving (respiratory) cycle in this example, the images may be acquired from a plurality of moving cycles instead. As long as there are provided a set of a plurality of CT images each associated with time and state information, the images are not limited to any single cycle.

After the reading of the 3D CT images from the data server 502 into the memory 604 has been completed and the images have been displayed on the display device 603, the operator using the input device 602 such as a mouse inputs the region to be designated as the target on slices of the 3D CT images, i.e., on each of the 2D CT images making up the 3D CT images. Here, the target region to be input is a region that has or may have tumor cells and is thus determined to be irradiated with a sufficient dose of radiation. As such, the region is called the target region. If there exists near the target region any critical organ for which the dose of radiation must be minimized or some other region that needs evaluation and control, the operator also designates the critical organs and other regions of interest.

The regions in the case above may be drawn either on all individual 3D CT images included in the 4D CT images or on a single 3D CT image representing one state included in the 4D CT images. For example, an image of the fully exhaled state may be selected and regions may be designated on that image. Meanwhile, the target region may be drawn on a single image synthesized from all images. For example, a plurality of 3D CT images are compared for CT values at points each representing the same position, and the highest of the values in intensity at all points are selected to obtain one set of synthesized CT images. Alternatively, the region may be drawn on images of a different modality typified by MRI (step 103).

Where the target region or the region of a critical organ is input solely on a single 3D CT image, the non-rigid registration technique may be used to determine the region on each of the 3D CT images included in the 4D CT images. There may be cases where corrections by the operator are necessary. In such cases, the shapes of the regions on a given image, including deformation of the target region, may be defined in terms of a moving model (directions and magnitudes of moments of the points) so as to draw the regions corresponding to the other images. This makes it possible to alleviate the workload on the operator by eliminating the need for drawing the regions on the individual 3D CT images included in the 4D CT images.

After inputting the regions of interest to all 3D CT images, the operator designates registration of the input regions. The registration causes the regions input by the operator to be stored as 3D position information into the memory 604 (step 104). The position information about the regions may also be stored into the data server 502. Upon reading of 3D CT images, the previously input information may be read along with the 3D CT images.

The operator then prepares the treatment plan that includes information about the positions and energy levels of the beams to be applied to the registered target region. Whereas 4D CT images include a plurality of 3D CT images holding information about the variations of the target region, the treatment plan is prepared by referencing one specific 3D CT image that is selected by the operator. The 3D CT image to be selected may be one of the 3D CT images which corresponds to one phase in the 4D CT images, or an ordinary (non-4D) 3D CT image obtained separately from the 4D CT images. The operations that follow will be carried out on the basis of the 3D CT image thus selected.

On the selected 3D CT image, the operator sets necessary irradiation parameters (step 104). The operator first sets the directions of irradiation. When the angle between the gantry 311 and the bed 407 is suitably selected, the particle therapy system to which this embodiment is applied can apply beams to the patient in any desired directions. A plurality of irradiation directions may be set on a single target. When the beam is applied in a given direction, the center of gravity of the target region 706 is supposed to be positioned to coincide with an isocenter (i.e., center of rotation of the gantry 311) during irradiation, as shown in FIG. 9.

The other parameters to be determined for irradiation by the operator are the doses with which to irradiate the regions registered in step 102 (prescription doses). The prescription doses include the dose with which to irradiate the target and the maximum dose permissible for the critical organs.

After the above parameters have been determined, the treatment planning system 501 automatically performs calculations under the direction of the operator (step 107 in FIG. 1). What follows is an explanation of detailed dose calculations performed by the treatment planning system 501.

First, the treatment planning system 501 determines beam irradiation positions. Where the above-mentioned discrete scanning method is adopted, the treatment planning system 501 calculates discrete spots; where continuous irradiation is to be used, the treatment planning system 501 calculates a scanning path. This embodiment is assumed to adopt the discrete scanning method. The irradiation positions are set to cover the target region. If a plurality of directions are designated as the irradiation directions (i.e., as angles between the gantry 311 and the bed 407), the treatment planning system 501 performs the same operation in each of the irradiation directions.

After all irradiation positions have been determined, the treatment planning system 501 starts calculating optimization of the irradiation doses. The dose with which to irradiate each spot is determined to approach the target prescription doses set in step 105. Widely adopted for use with this calculation is the method of utilizing an objective function that numerically represents the divergence between the irradiation dose per spot and a target prescription dose. The objective function is defined to become smaller the more the dose distribution fulfills the target dose. Calculations are repeated to search for the irradiation dose that minimizes the objective function, whereby an optimum irradiation dose per spot is obtained.

Upon completion of the repeated calculations, the irradiation dose necessary for each spot is ultimately determined. The sequence in which a plurality of spots are irradiated is also determined at this stage. Ordinarily, a zigzag path is established as indicated by a scanning path 806 in FIG. 5. It is also possible to rearrange the irradiation sequence in accordance with criteria that take scanning times and scanning directions into consideration. Still, if the discrete scanning method is adopted, the irradiation sequence does not affect the dose distribution at this stage.

The treatment planning system 501 then causes the calculation device 605 to calculate the dose distribution using the ultimately obtained spot positions and spot irradiation doses. If necessary, the display device 603 may display the result of the dose distribution calculations. It should be noted that this result corresponds to the 3D CT image selected in step 103 and does not reflect the information about the variations of the target region such as movements, deformation or rotation of the target during radiation irradiation.

The treatment planning system of this embodiment can calculate the dose distribution based on the prepared treatment plan information not only by use of a specific 3D CT image alone but also through integration of information about 4D CT images, i.e., information about different 3D CT images from different states, before displaying the dose distribution result. What follows is a detailed explanation of how the calculations are performed. The flow of the calculations is summarized by steps 201 through 210 in FIG. 2.

The treatment planning system 501 of this embodiment allows the state of tumor movements to be selected as desired at the time of starting the radiation treatment in accordance with the treatment plan.

First, the operator designates the state (phase) in effect at the start of irradiation, i.e., when radiation irradiation is started (step 106). As mentioned above, the individual 3D CT images contained in 4D CT images include information about the phases corresponding to the variations of the target region. For example, in the case of the 4D CT images including the respiratory movement information such as is shown in FIG. 9, one respiratory cycle is divided into four portions, i.e., the fully exhaled state, fully inhaled state, and intermediate states (phases), represented by the CT images 701, 702, 703, and 704 respectively. When the respiratory cycle is repeated in this sequence, it is possible to designate the phase states of the images by real numbers between 0 and 1, e.g., the state of the image 701 by a phase of 0, the state of the image 702 by a phase of 0.25, the state of the image 703 by a phase of 0.5, and the state of the image 704 by a phase of 0.75. The image 701 is reached again in the phase 1.0 following the phase 0.75 of the image 704. Designating different phases by real numbers between 0 and 1 is only an example. If there is some other benchmark easier to understand by the operator, that benchmark may be adopted instead.

The phases of the individual 3D CT images included in 4D CT images may be obtained beforehand by a device that acquires such 4D CT images. Alternatively, the operator may set the phases of the 3D CT images using the input device 602. If the operator using the input device 602 sets the phases regarding the variations of the target region with respect to a series of 3D CT images, these 3D CT images can be used by the treatment planning system 501 of this embodiment in place of the images obtained by a special imaging method, as discussed above.

Figure 10:
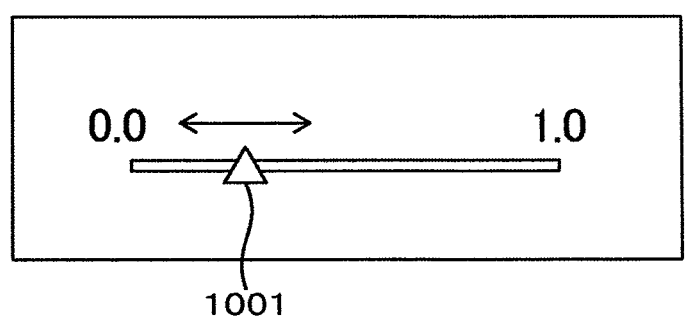
FIG. 10 is a schematic view showing a typical tool for establishing an initial phase.

The treatment planning system 501 of this embodiment is furnished with a phase designation function that allows the operator to designate the phase at the time of starting irradiation. For example, if there is provided a slider 1001 such as one shown in FIG. 10, the operator uses the input device 602 to adjust the slider 1001 in order to set the phase. Alternatively, the operator may directly input the value of the phase. If the operator does not input the phase value, a default value is set (step 202). Incidentally, the sequence formed by step 106 in which the initial phase is input, by step 104 in which the region is input, and by step 105 in which irradiation parameters are determined is not limited to what is shown in FIG. 1; these steps may be sequenced otherwise. Also, the input device 602 may double as a device that provides the phase designation function.

In accordance with the input phase at the start of irradiation and with a moving cycle in effect, the calculation device 605 allocates the phases corresponding to the time periods that elapse from the beginning of irradiation. That is, by associating the information about the elapsed time from beginning to end of the radiation treatment as per the treatment plan with the phases set for a series of 3D CT images making up the 4D CT images, the calculation device 605 makes it possible to reference the phase state the patient is in at a given point in time from the start of irradiation (step 203). Making this association requires information about the moving cycle included in the 4D CT images, i.e., information about the cycle of the variations of the target region. If the cycle is made known from information gained upon 4D CT acquisition, that information can be utilized. If the cycle is unknown, then the operator may use the input device 602 to input a typical value, such as a few seconds in the case of the respiratory cycle.

In another case, following the actual irradiation, the treatment planning system may be used to calculate the dose distribution for the purpose of evaluating the previously irradiated doses. In this case, if a device capable of monitoring tumor movements during radiation irradiation is used to record the tumor movements continuously from the start of irradiation, then changes of the tumor phase in elapsed time, i.e., the phases regarding the variations of the target region, may be directly input with respect to elapsed time.

Meanwhile, the calculation device 605 calculates information about the radiation (irradiation positions, irradiation directions, energy levels, etc.) applied at given points in time since the start of the radiation treatment in accordance with the treatment plan (step 204). Whereas the beam irradiation positions and irradiation doses are included in the treatment plan prepared in advance, calculating the irradiation positions corresponding to elapsed time requires such information as the irradiation time per spot, the time for movement from one spot to another, and the time required to change the energy level.

These items of information are specific to the radiation therapy equipment. In the case of particle beam scanning irradiation with this embodiment, the information includes the current value of the beam extracted from the synchrotron, the time required to change the energy level, and the scanning speed in effect when the scanning magnets 401 and 402 are used. These values are stored beforehand in the memory 604 of the treatment planning system and may be referenced when needed for calculations. The operator can also change these values.

Either of steps 203 and 204 may precede the other. By referencing the results of the calculations in steps 203 and 204, it is possible to obtain both the phase of the tumor and the information about the radiation being applied at a desired point in time since the start of irradiation. Based on these two items of information, the calculation device 605 calculates the dose distribution. In this case, certain values indicative of the phases regarding the variations of the target region (i.e., phase of the tumor) are determined corresponding to elapsed time. However, the 4D CT images include the information only about between a few and up to 10 phases per cycle (e.g., four phases in FIG. 9); there may or may not exist a CT image coinciding with a given phase.

In such a case, there may be conceived a method whereby, in calculating the dose distribution formed by the radiation applied to a given position, the CT image with the phase closest to the time at which that position is irradiated is selected. In this case, according to the scanning irradiation method, not all spots having the same energy level (e.g., spots within the plane 802 irradiated with the same energy level in FIG. 5) may be allocated to the same CT image. For example, the dose calculations may be performed on a CT image with different phases in the first and the second half thereof. As a result, when the ultimately calculated doses are evaluated, there may occur a region with its dose higher or lower than in practice along the boundary between the first and the second half of the image.

Meanwhile, it only takes dozens to hundreds of milliseconds to irradiate each spot with the same energy level. The time represents a speed sufficiently higher than that of the respiratory movement or the like. Essentially, the time for the irradiation seems hardly to affect the dose distribution regarding the movement. That is, according to the methods such as the scanning irradiation method for selecting the image of the closest phase, when the irradiation position is changed at short time intervals, there is a possibility that unexpected dose distribution changes will occur theoretically.

Figure 11:
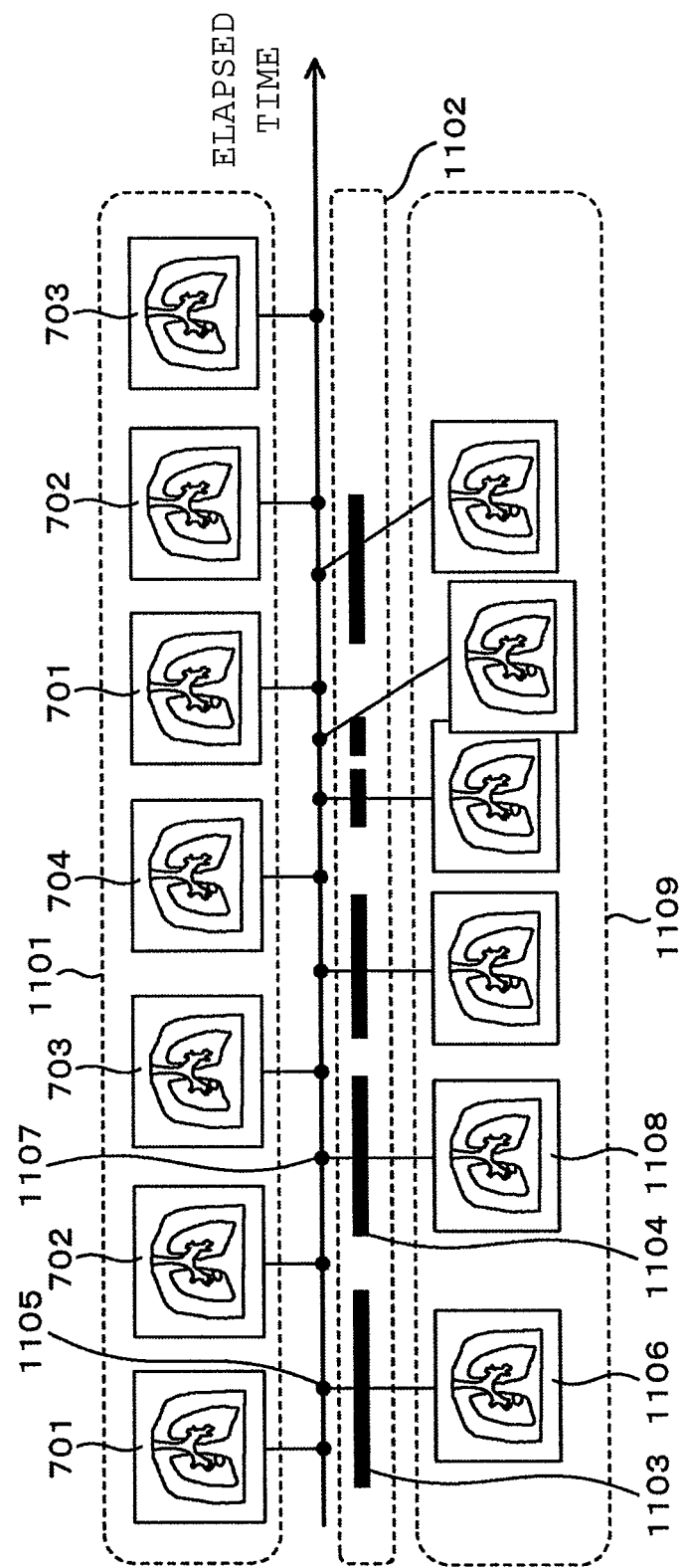
FIG. 11 is an explanatory view illustrating the concept of the present invention.

In order to avoid the above possibility, the treatment planning system of this embodiment performs dose distribution calculations using the method to be described below. FIG. 11 conceptually illustrates this method.

As mentioned above, the calculation device 605 can calculate the patient's phases as a function of elapsed time from the start of irradiation. FIG. 11 shows elapsed time on the horizontal axis and indicates, enclosed by broken lines, a result 1101 of 4D CT images having been associated with the elapsed time. The same cycle is assumed to be repeated so that the image 701 (phase 0) is followed by the image 702 (phase 0.25), followed by the image 703 (phase 0.5), followed by the image 704 (phase 0.75), and followed by the image 701 to again reach the beginning of the cycle.

Here, the calculation device 605 classifies the radiation used for the treatment into a plurality of groups (step 205). Where the scanning irradiation method is in use, each of the spots involved might be classified as one group in the case of the minutest classification. Usually, however, it is sufficient to classify the beams having the same energy level into one group. The latter way of classification is shown in the form of a result 1102 enclosed by broken lines in FIG. 11, the result 1102 associating each group with the corresponding elapsed time of irradiation. Irradiation times 1103 and 1104, each indicated by a solid line, represent the time in which the spots belonging to one group have all been irradiated.

The calculation device 605 then sets a representative irradiation time for each of the groups (step 206). For example, if the exact middle point (mid-period) of the time for irradiating the spots belonging to one group is regarded as a representative irradiation time point, it is easy to calculate that representative time point from the treatment plan. Based on that mid-period, the corresponding phase of the tumor is referenced.

As can be seen from FIG. 11, the above phase obviously does not coincide with any of the images (one of 701 through 704) included in the original 4D CT images. In FIG. 11, a representative time point 1105 of the irradiation time 1103 fails to coincide with the phases (of images 701 through 704) in the result 1101 from associating the 4D CT images with the elapsed time.

In such a case, the calculation device 605 generates the image corresponding to the phase in question using the images 701 through 704 included in the original 4D CT images.

In the example of FIG. 11, a 3D CT image indicative of the phase corresponding to the representative time point 1105 is generated from the images 701 and 702 that are adjacent to that phase (step 207). With this embodiment, as is evident from FIG. 11, the calculation device 605 interpolates the information about the variations of the target region for each of the periods in which radiation is applied so as to generate a 3D image reflecting the result of the interpolation.

The technique used here is non-rigid registration. The non-rigid registration technique involves associating points in the reference image with their corresponding points in other images. That is, point A with coordinates x on the image 701 is known to correspond with a point with coordinates x' on the image 702. Furthermore, a vector advancing from x to x' is defined. With the image 701 given the phase 0 and with the image 702 having the phase 0.25, if the phase is 0.1 of which an image is desired, the point corresponding to point A is identified by the coordinates obtained by extending from point A the defined vector for a length acquired by multiplying the original length by 0.1/0.25. This work is carried out on all points involved in order to generate the image with the phase corresponding to the representative time point 1105. This image generation method is only an example. Any other method may be adopted as long as it permits generation of a 3D CT image corresponding to the representative time point in the irradiation time between two 3D CT images.

In FIG. 11, an interpolated image 1106 is generated as the image with its phase corresponding to the representative time point 1105; likewise an interpolated image 1108 is generated as the image with its phase corresponding to a representative time point 1107 in the irradiation time 1104. Similarly generated CT images are shown as a group of interpolated images 1109 that have been generated through interpolation in keeping with the irradiation times. The dose distribution formed by the spots belonging to each group is calculated on the basis of these CT images. That is, the dose distribution formed by the spots belonging to the group irradiated in the irradiation time 1103 is calculated on the interpolated image 1106 resulting from interpolating the variations of the target region over the period in which radiation is applied to the spots belonging to the group in question. The calculation device 605 performs this work on all groups, i.e., on all irradiation times (step 208). In this manner, upon calculating the dose distribution, the treatment planning system of this embodiment generates an image reflecting the variations of the target region at a given time point in the elapsed time from beginning to end of the radiation treatment in accordance with the treatment plan, the image being generated by the process of interpolation from a plurality of previously acquired images, the system further calculating the dose distribution on the image thus generated.

Incidentally, the display device 603 may successively display the 3D CT image which is generated from the series of 3D CT images constituting the 4D CT images and which corresponds to the period in which radiation is applied, as well as the dose distribution calculated on the 3D CT image thus generated. This makes it possible chronologically to grasp the dose distribution formed when the radiation treatment is performed in accordance with the treatment plan.

After completing the dose distribution calculations of all spots, the calculation device 605 integrates the dose distributions calculated on all images in order to obtain the ultimate dose distribution. That is, the calculation device 605 integrates the dose distributions formed in each of the time periods in which radiation is applied from beginning to end of the radiation treatment, thereby calculating the dose distribution to be formed upon completion of the radiation treatment.

In FIG. 11, given the CT images within the interpolated image group 1109 generated through interpolation in keeping with the irradiation time, the dose distribution of each spot in the corresponding group is calculated. All dose distributions in the group are thus integrated (step 209). The non-rigid registration technique may be used to integrate the doses at the corresponding points. The calculation device 605 displays the ultimate dose distribution on the display device 603.

The operator evaluates the output dose distribution to be formed upon completion of the radiation treatment, and determines whether the dose distribution satisfies the desired degree of coincidence with the target dose distribution (step 109). For purpose of evaluation, it is also useful to perform the calculations all over again by changing the initial phase designated in step 105. Alternatively, there may be provided a calculation means which, after a number of initial phases have been automatically selected and calculated, calculates a mean value of the divergences of these phases from their target distributions. When the calculation device 605 calculates the mean value of the divergences between the dose distributions of the established initial phases on the one hand and the target dose distribution on the other hand, it is possible to evaluate the average effect of the variations of the target region on the planned dose distribution.

Also, the treatment planning system 501 of this embodiment may get the display device 603 to display not only the dose distribution on the 3D CT image but also the dose distribution on a desired cross section. It is also possible to display graphically a dose histogram within a specific region typified by the target region. If necessary, the operator using the input device 602 may output the displayed distributions and graphs as data out of the treatment planning system 501.

Upon evaluating the ultimately formed dose distribution, the operator might conclude that the dose distribution is not acceptable. In that case, step 103 is reached again and the irradiation parameters are again set. The parameters to be changed include the irradiation directions and prescription doses. The scanning path and repeat irradiation count can also be set because these values affect the dose distribution where 4D CT images are used in the calculations.

After the settings have been changed, the calculations using the 4D CT images are repeated. When the desired result is obtained, the preparation of the treatment plan is terminated. The irradiation conditions thus obtained are stored into the data server 501 via the network (steps 110 and 111).

As described above, the treatment planning system 501 of this embodiment can evaluate, using 4D CT images, the ultimately formed dose distribution by taking into account how the movements of the target affect the dose distribution.

The calculation device 605 interpolates the information about the variations of the target region for each of the time periods in which radiation is applied in accordance with the treatment plan information. As a result of the interpolation, the calculation device 605 generates from the 4D CT images a 3D CT image reflecting the variations of the target region in the irradiation period. By calculating the dose distribution using the 3D CT image thus generated, it is possible to provide highly accurate dose distribution calculations taking the movements and deformation of the target region into consideration.

Second Embodiment

With the first embodiment, as shown in FIG. 11, the image corresponding to each of the phases involved is generated through the operation of interpolation using the non-rigid registration technique. When the number of images to be generated increases, so does the time required for calculations. Because the operation of generating CT images spontaneously interpolate the pixels of the image portions that are not necessary to calculate the dose distribution, the second embodiment aims at limiting the calculations only to the regions relevant to the dose distribution such as the target region.

Figure 12:
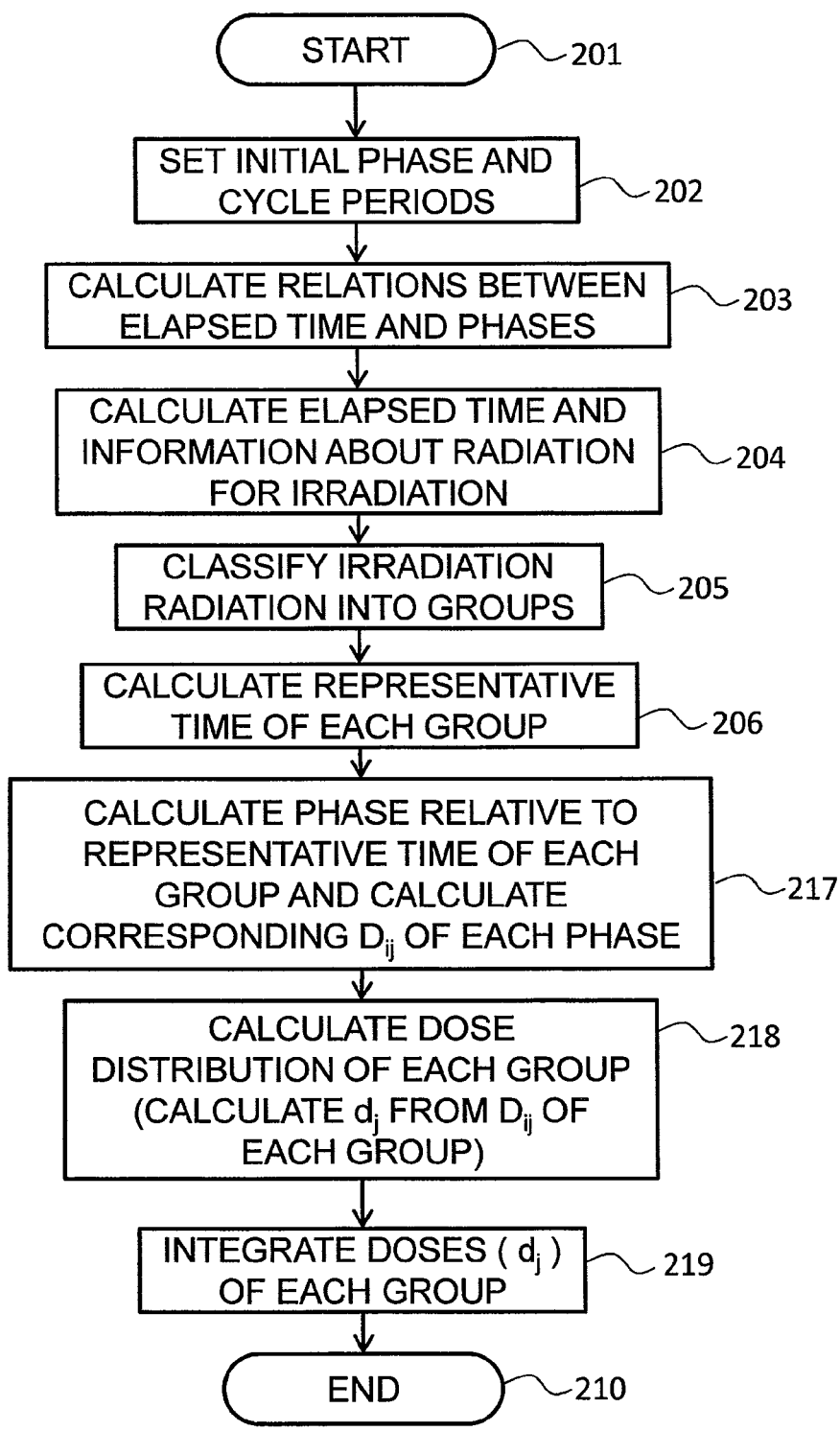
FIG. 12 is a flowchart showing a flow of operations performed by a treatment planning system as a second embodiment of the present invention.

In this embodiment, the flow of operations to be performed by the operator as shown in FIG. 1 is the same as with the first embodiment. The flow of detailed calculations shown in FIG. 2 is also the same as with the first embodiment up to step 206. Only the details of step 217 to step 219 are different from the first embodiment as shown in FIG. 12 and are thus explained hereunder.

Consider calculating the dose distribution regarding the spots belonging to one of the groups derived from the classification in step 205. First, calculation points are set inside the region of interest such as the target region input by the operator in step 103. The calculation points need only be arranged inside the region at the resolution of the 3D CT image and may be set either by the operator using the input device or by the calculation device 605 automatically within the target region.

The index for these calculation points may be represented by reference character j. What is then calculated is the dose to be given to a j-th calculation point when an i-th spot among the spots belonging to the group of interest is irradiated with the beam having a unit intensity. The value thus calculated is represented by $D_{ij}$. This value is calculated for all spots and all calculation points in step 217 shown in FIG. 12. That is, $D_{ij}$ denotes the degree of the dose received by the calculation point j from each of the spots irradiated with the beam having a predetermined intensity (i.e., unit intensity beam) in the 3D CT image retaining the phase of a given variation of the target region.

The dose $d_j$ of the j-th calculation point is calculated using the following expression that adds up the contributions from surrounding spots to the calculation point in question. This process is performed in step 218 shown in FIG. 12.

It explains in detail about step 217 of the present embodiment.

$$d_j = \sum_i D_{ij} w_i \quad (1)$$

where, $w_i$ represents the irradiation dose applied to the i-th spot.

The calculation device 605 calculates $D_{ij}$ for all 3D CT images included in the 4D CT images (step 217). That is, with regard to each of the series of 3D CT images constituting the 4D CT images, the calculation device 605 calculates the degree of the dose given to the calculation point j when the inside of the target region is irradiated with the radiation having a predetermined energy level. In this embodiment, in the example of FIG. 9, the 4D CT images include four image sets 701 through 704 that are referenced successively by the calculation device 605 as A, B, C and D, respectively. For example, the element $D_{ij}$ calculated by use of the image 701 is expressed as $D_{ij}^A$, and the element $D_{ij}$ calculated using the image 702 is expressed as $D_{ij}^B$.

On the basis of the above information, the dose at the calculation point on the image corresponding to a given phase is obtained as follows: Let the phase of the image 701 be 0 and let the phase of the image 702 be 0.25, as with the first embodiment. The dose on the image corresponding to the phase 0.1 is calculated not by interpolating the entire 3D CT image as in the case of the first embodiment but by interpolating the values of $D_{ij}$. That is, a new value of $D_{ij}$ is calculated using the following expression:

$$D_{ij} = \frac{0.25 - 0.1}{0.25} D_{ij}^A + \frac{0.1}{0.25} D_{ij}^B \quad (2)$$

Next, it explains about step 218.

The newly acquired $D_{ij}$ is the result of interpolating the contributions of the dose given to the calculation point j by the entire target region, from the series of 3D CT images and from the elapsed time of a radiation treatment, at a given time point in the radiation irradiation period since the start of the radiation treatment in accordance with the treatment plan. That is, whereas the first embodiment generates the 3D CT image as a result of interpolating the information about the variations of the target region in the radiation irradiation period, the second embodiment calculates the contributions of the dose given to the calculation point j.

The dose at each calculation point in the region of interest can be calculated from the expression (1) above using the value obtained by the expression (2). In the elapsed time from beginning to end of the radiation treatment according to the treatment plan, the calculation device 605 interpolates $D_{ij}$ at a given point in the radiation irradiation period based on the expression (2), reads from the treatment plan the dose $w_i$ of radiation applied at that point in time, and calculates the expression (1) to obtain the dose corresponding to the calculation point j at that point in time (step 218).

As with the first embodiment, because the calculation device 605 integrates the doses at the calculation point j from beginning to end of the radiation treatment in accordance with the treatment plan as shown in step 219 of FIG. 12, it is possible to evaluate the dose distribution to be formed upon completion of the radiation treatment. The integrated dose distribution can also be displayed on the display device 603.

When the operations above are carried out, it is possible to skip the operation of interpolating the 3D CT image corresponding to the radiation irradiation period using the non-rigid registration technique or the like. This shortens the time required for calculations and makes it possible to calculate the dose distribution reflecting the information about the variations of the target region. As long as the phase intervals between the 3D CT images included in the original 4D CT images are not inordinately wide, the method of the second embodiment provides substantially the same calculation results as the first embodiment.

Third Embodiment

With the second embodiment, it was necessary to calculate $D_{ij}$ of all phases for all spots and all calculation points. The amount of the calculations to be performed becomes greater the larger the target and the larger the number of the phases involved. A third embodiment of this invention aims to narrow down the necessary calculations for a reduction in the amount of the calculations.

Figure 13:
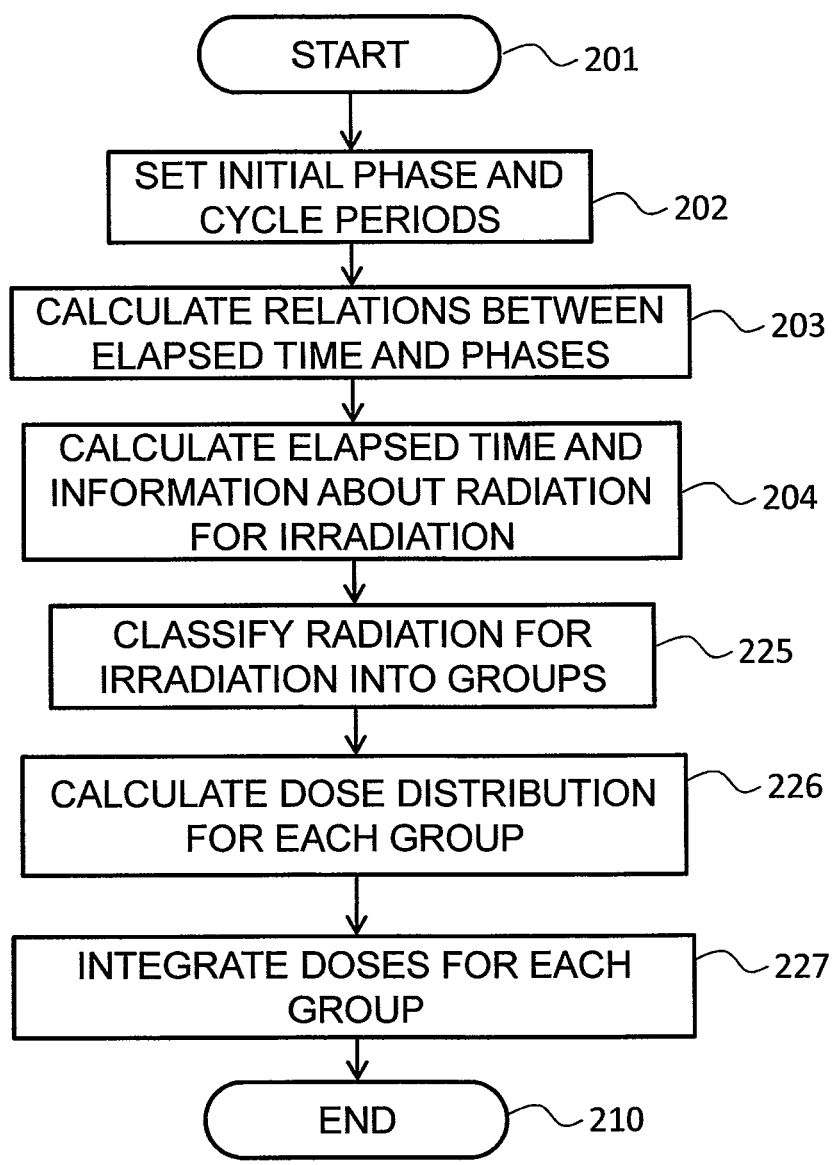
FIG. 13 is a flowchart showing a flow of operations performed by a treatment planning system as a third embodiment of the present invention.

The flow of the operating steps performed by the operator with the third embodiment is substantially the same as with the first embodiment shown in FIG. 1. The detailed calculations with the third embodiment are the same up to step 204 in FIG. 2 showing the flow of steps of detailed calculations with the first embodiment. It is step 205 and subsequent steps that are different from those of the first embodiment. FIG. 13 shows a flow of detailed calculations carried out by the third embodiment.

Figure 14:
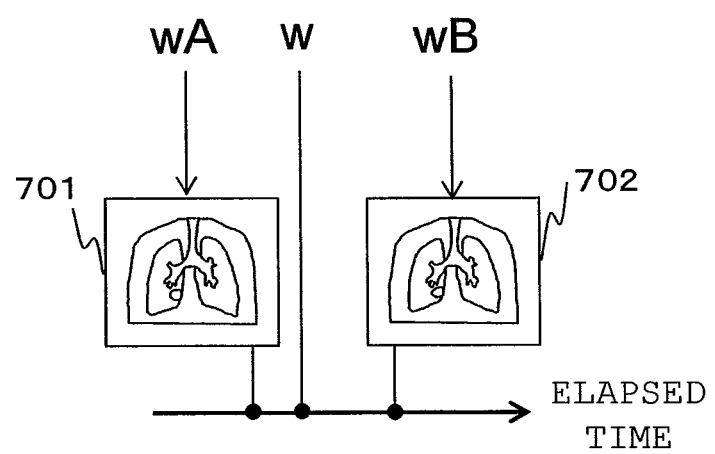
FIG. 14 is a conceptual view showing how processing is performed by the treatment planning system as the third embodiment.

In step 225 of FIG. 13, all spots are classified into groups by phase. Given the 4D CT images such as those in FIG. 9, the images 701 through 704 are assumed to be assigned corresponding groups A, B, C and D, respectively. Suppose now that a given spot is selected, that the irradiation dose for that spot is represented by w and that the phase in which the spot is irradiated is 0.1. That phase is obtained in steps 203 and 204. That is, the phase in which the spot is irradiated can be acquired from the relations calculated in step 203 between the phases of the 4D CT images and the elapsed time from the beginning of irradiation, and from the elapsed time from the beginning of irradiation at the point in time at which the spot calculated in step 204 is irradiated. As shown in FIG. 14, the phases preceding and succeeding the spot are group A and group B of which the phases are 0 and 0.25, respectively. The irradiation dose w for that spot is linearly distributed to group A and group B. An irradiation dose wA=w (0.25-0.1)/0.25) is distributed to group A, and an irradiation dose wB=w (0.1/ 0.25) is distributed to group B. The distribution above is repeated for all spots. Because each spot is divided into a preceding spot and a succeeding spot, the number of spots to be calculated is doubled.

Although the distribution ratio is assumed to be linear with the third embodiment, a specific group or groups may be weighted for the distribution. Calculating the distribution ratio is not limited to the above-described method.

In step 226, the dose distribution is calculated for each group. That is, the dose distribution for the spots belonging to each group is calculated on the corresponding image. For example, the dose distribution for the spots belonging to group A is calculated based on the image 701. The result of the dose distribution thus calculated is integrated for each group.

In step 227, the dose distributions calculated in step 226 are all integrated. Since the images 701 through 704 represent different states in the body, it is necessary to calculate the corresponding positions between the images using the non-rigid registration technique. It is also necessary to decide on the image serving as the reference for dose distribution integration. For example, if the image 701 is selected as the reference, those points in the images 702 through 704 that correspond to a calculation point jA in the image 701 may be assumed as jB, jC and jD, respectively. The points jB, jC and jD are calculated by the non-rigid registration technique. When the dose value at the point jA calculated for group A in step 226 and the dose values at the points jB, jC and jD are all integrated, the ultimate dose value at the point jA can be obtained. These calculations are performed for all calculation points.

As described in the above steps, it is possible to calculate the dose distribution of the moving target by performing the dose distribution calculations on each spot for only two phases. There is no need to carry out dose distribution calculations for all phases, so that the dose distribution of the moving target can be calculated with a limited memory capacity over a shorter time period.

Incidentally, the range in which to calculate the dose distribution may be limited to inside the target or to the entire dose distributions. When the dose calculations are limited within the target alone, the calculations can be repeated efficiently in such cases as where the initial phase is varied.

Furthermore, the first embodiment and the third embodiment may be used in combination. For example, intermediate images may be prepared for each of the images 701 through 704 so as to multiply the number of images by a factor of 2 or more. When the dose distribution is to be calculated, the irradiation dose for each spot may be grouped into the images corresponding to the preceding and succeeding phases following the image multiplication. This makes it possible to calculate more accurate dose distributions while reducing the amount of the calculations involved.

What is claimed is:

1. A treatment planning system comprising:
 a computer, including a processor and a memory, coupled to a particle beam therapy system;
 an input device coupled to the computer;
 a display device, coupled to the computer, which displays information of a treatment plan calculated by the computer;
 a storage unit, coupled to the computer, which stores a series of three-dimensional CT images that include information of variations of a target region to be irradiated with radiation of the particle beam therapy system,
 wherein the memory stores irradiation parameters input via the input device for irradiating the target with the radiation of the particle beam therapy system,
 wherein the computer is programmed to:
 associate the three-dimensional CT images of the series of three-dimensional CT images with information relating to time that has elapsed from a beginning to an end of a radiation treatment based on the calculated treatment plan,
 interpolate the information of the variations of the target region based on the information relating to the elapsed time and based on the series of three-dimensional CT images for each time period during which the radiation is to be applied, and
 calculate a dose distribution based on the interpolated information of the variations of the target region.

2. The treatment planning system according to claim 1, wherein the computer device generates a three-dimensional CT image reflecting the variations of the target region for the time periods during which the radiation is to be applied based on the series of three-dimensional CT images associated with the information relating to the elapsed time,
 wherein the computer calculates the dose distribution on the generated three-dimensional CT image.

3. The treatment planning system according to claim 1, wherein a calculation point is established within the target region included in the series of three-dimensional CT images either through input via input device or calculation by the computer, and
 wherein, when the target region is irradiated with radiation of a given energy level, the computer calculates a contribution of the dose given to the calculation point for each of the three-dimensional CT images constituting the series of three-dimensional CT images,
 wherein the computer thereafter calculates as the interpolated information of the variations of the target region the contribution of the dose given to the calculation point over the time periods during which the radiation is to be applied in accordance with the treatment plan based on the dose contribution calculated to be given to the calculation point for each of the three-dimensional CT images constituting the series of three-dimensional CT images, and
 wherein computer further calculates the dose distribution based on the result of the calculations.

4. The treatment planning system according to claim 2, wherein the display device displays the generated three-dimensional CT image and the dose distribution calculated on the generated three-dimensional CT image.

5. The treatment planning system according to claim 1, wherein the computer interpolates the information of the variations of the target region at an intermediate time point of each of the time periods during which the radiation is to be applied.

6. The treatment planning system according to claim 1,
 wherein the computer calculates the dose distribution to be formed upon completion of the radiation treatment by integrating the dose distribution formed over each of the time periods during which the radiation is applied from the beginning to the end of the radiation treatment, and
 wherein the display device displays the dose distribution formed upon completion of the radiation treatment.

7. The treatment planning system according to claim 6, wherein the computer compares the dose distribution calculated to be formed upon completion of the radiation treatment with the target dose distribution to be formed upon completion of the radiation treatment, and wherein the display device displays the result of the comparison.

8. The treatment planning system according to claim 1, wherein the input device establishes a phase regarding the variations of the target region with respect to each of the three-dimensional CT images constituting the series of the three-dimensional CT images, a phase regarding the variations of the target region at a point in time at which the radiation treatment is started in accordance with the treatment plan, and a cycle of the variations of the target region, and wherein, based on the phase regarding the variation of the target region at the point in time at which the radiation treatment is started in accordance with the treatment plan and on the cycle of the variations of the target region, the computer associates the phase regarding the variations of the target region established regarding each of the three-dimensional CT images with the information relating to the elapsed time, the computer further interpolates the information about the variations of the target region over each of the time periods during which the radiation is applied based on the associated phases.

9. The treatment planning system according to claim 8, wherein the computer establishes a plurality of phases regarding the variations of the target region at the point in time at which the radiation treatment is started in accordance with the treatment plan, the calculation device further calculating the dose distribution to be formed upon completion of the radiation treatment regarding each of the plurality of phases.

10. The treatment planning system according to claim 1, wherein the computer distributes the amount of the radiation to the series of three-dimensional CT images based on the series of three-dimensional CT images associated with the information relating to the elapsed time and on the information relating to the elapsed time during which the radiation is to be applied, the computer further calculates the dose distribution on the series of three-dimensional CT images.

11. The treatment planning system according to claim 1, wherein the computer is further programmed to store the calculated dose distribution in the storage unit, and wherein the target is irradiated by the particle therapy system according to the calculated dose distribution.

\* \* \* \* \*